United States Patent [19]

Seddon

[11] Patent Number: 5,494,349
[45] Date of Patent: Feb. 27, 1996

[54] BONE CEMENT MIXING DEVICE

[75] Inventor: Peter Seddon, Stanley Pontlarge, England

[73] Assignee: Summit Medical Ltd., Bourton on the Water, England

[21] Appl. No.: 244,642

[22] PCT Filed: Dec. 4, 1992

[86] PCT No.: PCT/GB92/02259

§ 371 Date: Aug. 22, 1994

§ 102(e) Date: Aug. 22, 1994

[87] PCT Pub. No.: WO93/10892

PCT Pub. Date: Jun. 10, 1993

[30]   Foreign Application Priority Data

Dec. 6, 1991 [GB]  United Kingdom ............... 9126011

[51] Int. Cl.$^6$ ................................................. B01F 7/16
[52] U.S. Cl. .................................... 366/139; 366/288
[58] Field of Search ........................... 366/139, 602, 366/244, 279, 287, 288

[56]           References Cited

U.S. PATENT DOCUMENTS

| | | | |
|---|---|---|---|
| 3,640,510 | 2/1972 | Lea | 366/139 |
| 4,079,917 | 3/1978 | Popeil | 366/288 |
| 4,185,072 | 1/1980 | Puderbaugh . | |
| 4,721,390 | 1/1988 | Lidgren | 366/139 |
| 4,961,647 | 10/1990 | Coutts . | |

FOREIGN PATENT DOCUMENTS

| | | |
|---|---|---|
| 2597321 | 10/1987 | France . |
| 178572 | 4/1922 | United Kingdom . |
| 517340 | 1/1940 | United Kingdom . |

OTHER PUBLICATIONS

Patent Abstracts of Japan vol. 1, No. 118 (M-78)(3800) 8 Oct. 1977.
Patent Abstracts of Japan No. 53,088,259 (Tokyo Denki) 8 Mar. 1978.
International Search Report from European Patent Office, Mar. 9, 1993.

Primary Examiner—Robert W. Jenkins
Attorney, Agent, or Firm—Chilton, Alix & Van Kirk

[57]           ABSTRACT

An orthopaedic bone cement mixing device comprising a mixing bowl (1) and a lid (3), said lid (3) having a handle (4) extending outwardly therefrom. A mixing paddle (7) comprising a shaft (8) and vanes (9) extending outwardly therefrom extends into the bowl (1) from the lid (3) and is anchored in a groove (10) running around the base (2) of the bowl. A step-up gear mechanism (5, 11) is provided between the paddle (7) and the lid (3) such that, as the handle (4) is rotated the lid (3) rotates, causing the paddle (7) to rotate around the bowl (1). The drive wheel (5) of the gear mechanism is also caused to rotate and drives the driven wheel (11) which causes the shaft (8) of the paddle (7) to rotate about its own axis as the paddle (7) moves around the bowl (1).

14 Claims, 5 Drawing Sheets

BONE CEMENT MIXING DEVICE

The present invention relates to a device for mixing orthopaedic bone cement or the like.

Orthopaedic bone cement is used throughout the world to secure hip, knee and other metallic prostheses in an appropriate anatomical position. The bone cement is produced by thoroughly mixing together two components, usually methylmethacrylate monomer liquid and polymethylmethacrylate powder. The mixing is usually carried out using a simple bowl and spatula. The surgeon then removes the required amount of cement and manipulates it by hand before inserting it into a preformed cavity or applying it to a resected bony surface where the prosthesis is to be positioned. Cement may either be applied by hand or may be put into a syringe and applied thereby. However, this simple mixing method has two major drawbacks.

Firstly, free methylmethacrylate fumes are emitted from the mixture. It is desirable to remove these fumes, or prevent them from escaping into the atmosphere, since they have an unpleasant odour and may be harmful to operating room personnel. The fumes are known to cause nausea and giddiness and are generally objectionable, particularly to the nurses who actually carry out the mixing. Recently there has also been concern that long term exposure to these fumes results in a more serious health risk. Current employment law relating to occupational health means medical staff must now be protected against the exposure to hazardous substances.

Secondly, a very high mixing efficiency is required to produce a homogenous cement material. During the mixing process air is naturally introduced into the mixture since air is inherently existent within the powder and also in and around the mixing vessel. Air bubbles are also produced by the "boiling off" of monomer which occurs during the mixing process. The introduction of air produces a weak cement and, since the joint must usually support a heavy load, it is important to reduce the amount of air in the mixture as much as possible in order to improve the mechanical strength of the cement material.

In order to eliminate as much air as possible from the mixture mixing is now preferably carried out under vacuum. This considerably reduces the amount of air in the mixture. Mixing in a conventional bowl and spatula system can produce a product with a porosity value of approximately 20 to 25%. In a vacuum mix, the porosity is often reduced to levels below 5%.

Several devices for mixing the cement in a vacuum are presently available. The most successful of these combine a mixing chamber with a syringe. For example, EP-A-0178658 discloses a device for mixing bone cement comprising a mixing container connected to a feed device. A vacuum source is connected to the feed device for mixing the substances under vacuum. This device has proved to be a very efficient mixing and transfer system and eliminates the need to transfer the mixed cement from the mixing bowl to a syringe, which can be messy and time consuming and may expose the mixture to more air entrapment.

However, these combined mixer/syringe devices are expensive. Further, they are restricted to applying the cement by a syringe, whereas the majority of surgeons prefer to "hand pack" the cement. Bowl mixing also tends to be preferred by nurses who are used to the convenience of mixing in this vessel; a bowl is easier to use and it is important that the nurses feel confident since timing is very crucial and the mixture must be 'right first time'. Mixer/syringe devices may, therefore, have more potential for failure. Surgeons also tend to prefer bowl mixers because they can easily take samples of the cement from the bowl at any time to determine the progress of polymerisation as it is crucial that the mixture does not begin to set before it is applied.

Thus, the mixer/syringe devices have practical and economical limitations and a bowl mixer is a more attractive option.

Bowl mixing devices have been proposed which comprise a mixing bowl with a lid. A mixing paddle extends from the lid into the bowl and is rotated by means of a handle on the outside of the lid. A vacuum source is connected to the bowl to create a vacuum in the mixing bowl. However, this device has been found to be inadequate in that 'dead spots', i.e. areas where the components are not sufficiently mixed, occur, particularly in the middle of the bowl. There may also be a tendency for mixing paddles to break when faced with the challenge of a high viscosity material.

Problems have also arisen with regard to the capacity of known mixers. Several different types of cement are commonly used in Orthopaedic applications and it is desirable that a mixer should have the capacity to mix a sufficient quantity of any of these types. In particular, some of the cement used in the USA may be more bulky than the other cements and it has been found that known mixers cannot mix sufficient quantities efficiently, especially if larger amounts of cement are required such as in a revision operation which may require a triple mix.

According to one aspect of the present invention there is provided a hand-held mixing device for bone cement or the like, comprising an enclosed mixing chamber, a port in a wall of said chamber for connection to a vacuum source in use to enable a vacuum to be created in said chamber, a mixing paddle extending into said chamber, and a rotatable handle coupled to said paddle by a gear mechanism arranged such that rotation of said handle causes said paddle to rotate about its own axis and also moves the axis of rotation of the paddle within the chamber whereby the paddle is moved around substantially the entire cement containing region of the interior of the chamber.

By means of this arrangement an improved mixing action may be achieved in e.g. a bowl type mixing device which mixes the cement thoroughly and can be used more effectively than known devices to mix both small and large quantities of cement.

In a particularly preferred embodiment, the gear mechanism is a step-up gear such that a single rotation of the handle produces a plurality of rotations of the paddle about its own axis. Whilst the drive mechanism for moving the axis within the chamber may vary, as indeed may the path of such movement, it is preferred that the pivot axis is coupled to the handle in such a way that it describes a circle with each rotation of the handle causing a single planetary rotation of the pivot axis about the axis of rotation of the handle. It is preferable, on the other hand, that the number of stepped up rotations of the paddle about its own axis produced by a single rotation of the handle is not a whole number so that the paddle ends up in a different orientation after each turn of the handle to increase the mixing efficiency and avoid dead spots.

In order to reduce the amount of air in the mixture, and to prevent noxious fumes escaping, the chamber should preferably be completely sealed from the surrounding environment when in use.

A preferred structure comprises a hand-held mixing bowl with a removable lid which fits over the bowl and can preferably be locked to ensure the lid is held securely on the bowl during mixing. The handle is rotatably mounted in the lid and extends outwardly therefrom to be rotated by the user. A seal may also be provided between the lid and the rim of the bowl to ensure that the mixing chamber is completely air-tight and that no fumes can escape.

The form of the gear mechanism may vary. In a preferred embodiment, the paddle is carried by an axle which is eccentrically coupled to the handle as discussed. A circular rack fixed to the underside of the lid, and arranged coaxially with the rotation axis of the handle, drivingly co-operates with a cog wheel associated with the paddle to rotate the paddle as the handle is turned. Such an arrangement minimises the number of moving parts required.

Most thorough mixing is provided by a mixing paddle comprising a shaft and a plurality of vanes extending outwardly from the shaft. At least one vane should, for best results, extend out to the edge of the bowl and conform to the shape of the interior of the bowl; other vanes may extend into the bowl by different amounts. However, since the paddle both moves around the bowl and rotates about its own axis, even a single vane could provide thorough mixing in smaller systems.

As the cement is mixed it begins to thicken and this may cause the mixing vane to bend. To overcome this, a guide groove may be provided in the base of the mixing bowl in which the base of the paddle, or its axle, is supported as it rotates around the bowl. This groove anchors the paddle and keeps it upright even when the cement thickens.

Since every mixture will have slightly different characteristics and will begin to set at different times and since different circumstances often require cements at different stages of setting it is preferable that the surgeon can observe the cement during mixing without interrupting the mixing process or exposing the cement to air. Therefore it is preferable that the bowl is transparent or has a transparent window through which the cement can be observed.

In a preferred embodiment, gases emitted from the mixture are drawn off through a valve and filter arrangement which may comprise a separate, one-way valve and a charcoal filter, or an integrated valve/filter comprising a fibre material impregnated with activated charcoal. Such a filter means itself represents a new departure.

The outlet port for evacuating the chamber may be provided in the bowl or in the lid in the preferred embodiment, and preferably includes a male push fit or other connector for engagement in use with a hose leading to a vacuum pump.

According to another aspect of the invention there is provided a mixing system for bone cement or the like comprising a mixing chamber, a mixing paddle extending into said chamber, a handle rotatably mounted with respect to said chamber, said handle being connected to said paddle to cause rotation of said paddle, means for evacuating air from said chamber comprising a port in a wall of said chamber and a vacuum pump connected to said port, filter means adapted to remove unwanted fumes from air removed from said chamber, said filter means comprising either an activated charcoal medium or non-woven fibre material impregnated with a filtering substance such as activated charcoal.

Viewed from a further aspect the invention provides a mixing system for bone cement or the like comprising an enclosed mixing chamber communicating with a vacuum pump for removing air from the chamber in use, and a mixing mechanism comprising a mixing paddle driven by a handle which causes rotation of the paddle about an axis and simultaneously causes movement of the axis within the chamber.

Viewed from a still further aspect the invention provides a method of mixing bone cement or the like within an evacuated environment, which comprises moving the axis of a rotating mixing element within the mixture during mixing.

A preferred embodiment of the invention will now be described by way of example only and with reference to the accompanying drawings wherein.

Figure 1:
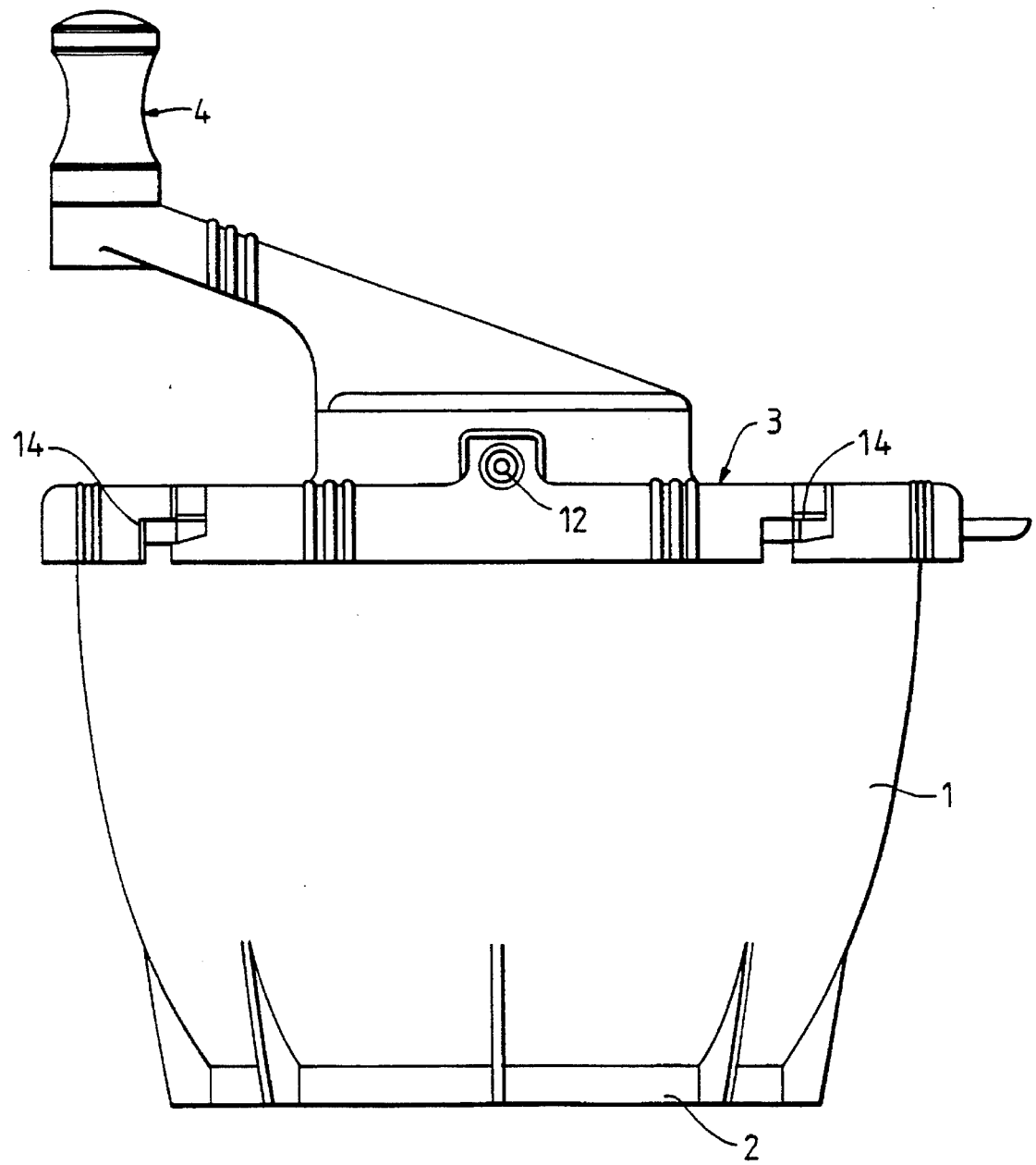
FIG. 1 shows a perspective view of a bone cement mixing device according to the present invention.
Figure 2:
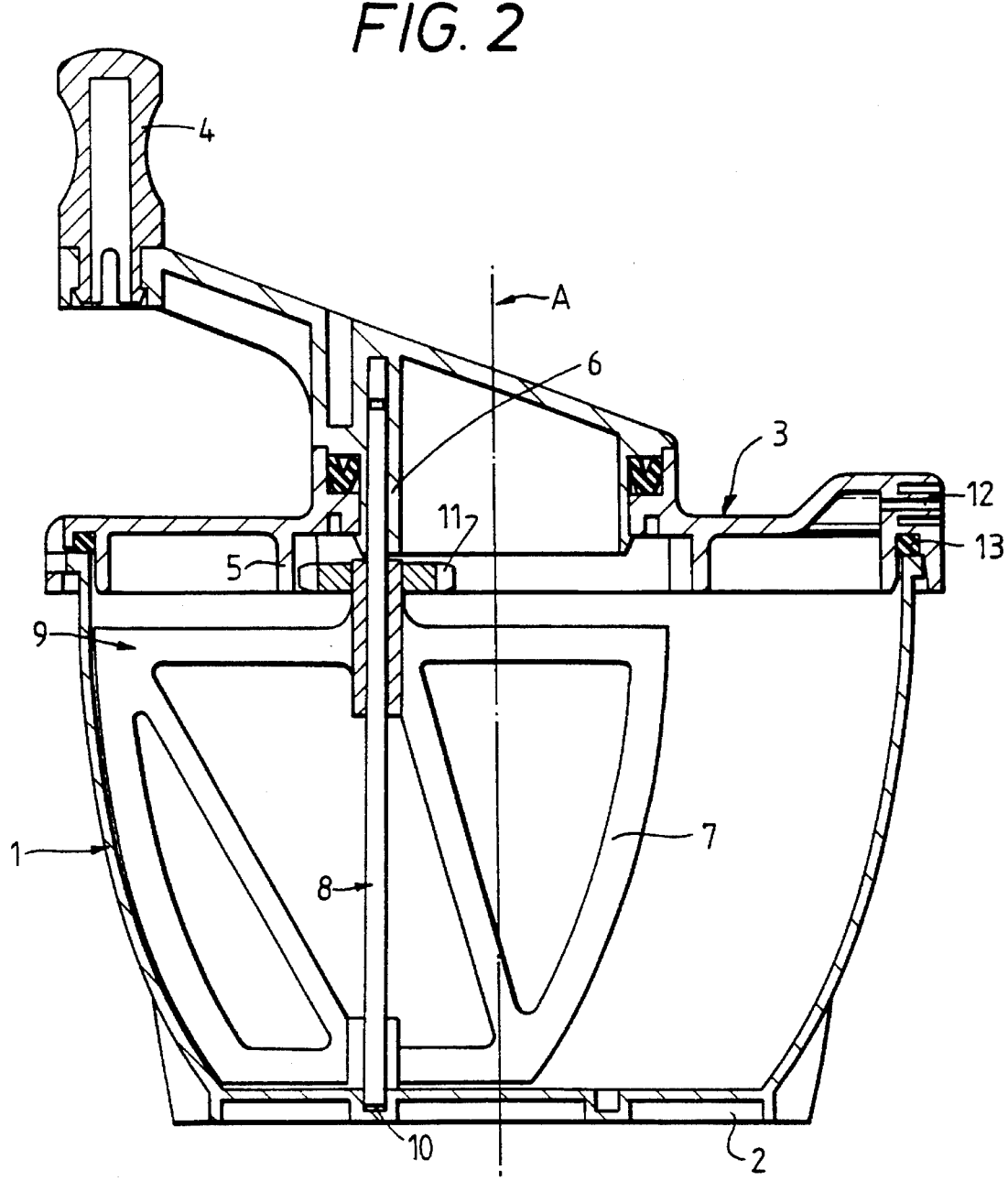
FIG. 2 shows a cross-section of the device of FIG. 1.
Figure 3:
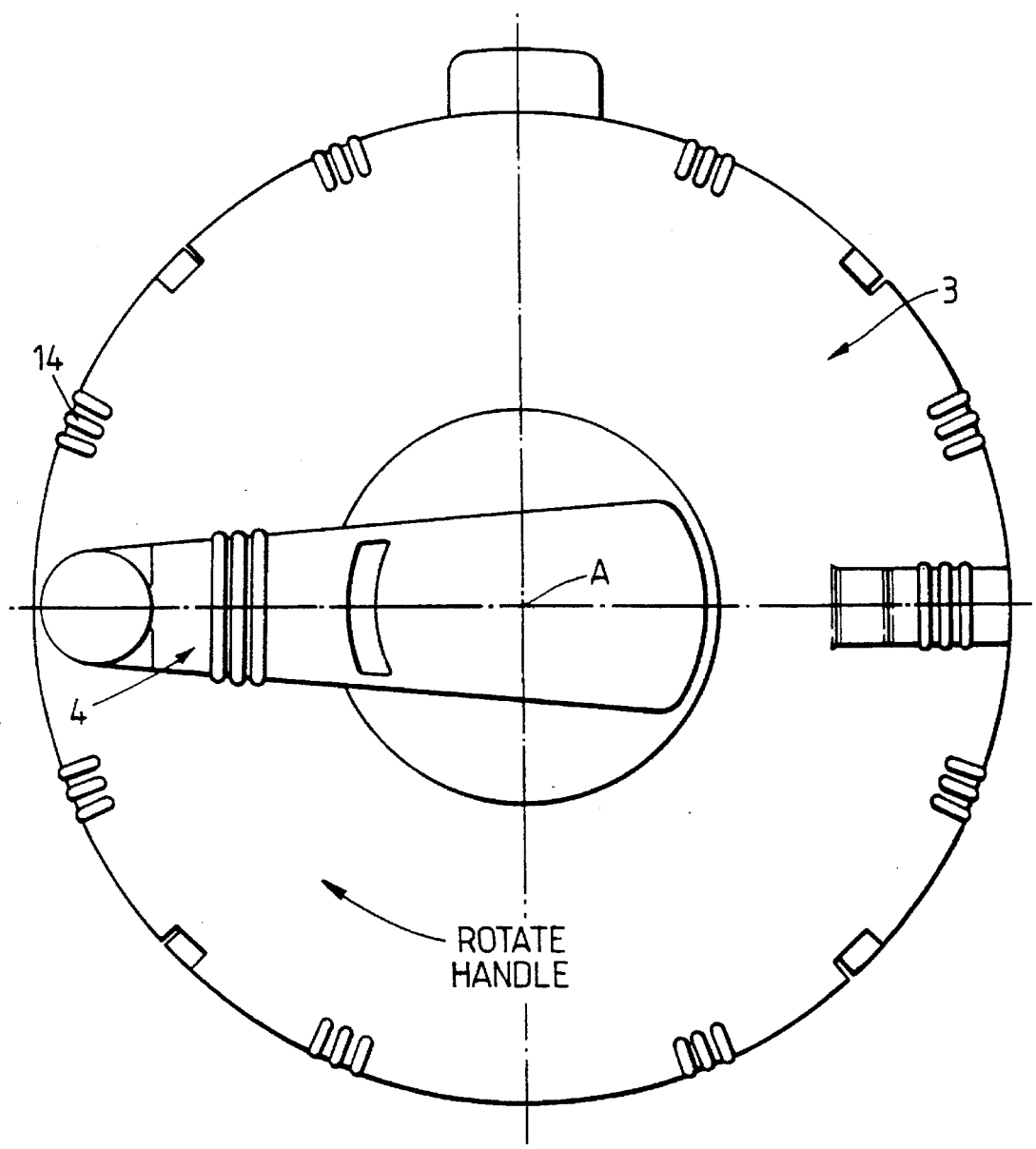
FIG. 3 shows a plan view of the device of FIG. 1.
Figure 4:
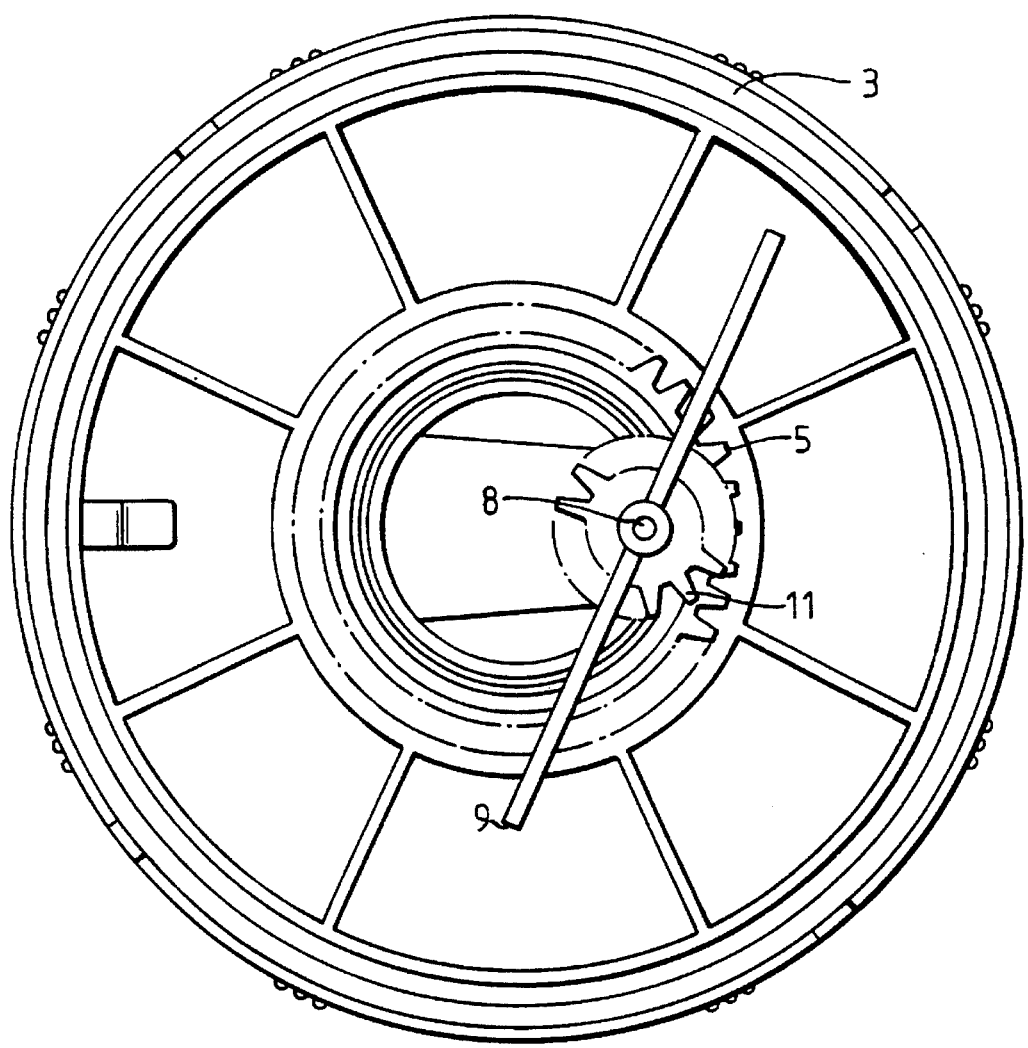
FIG. 4 shows the gear mechanism of the device of FIG. 1.
Figure 5:
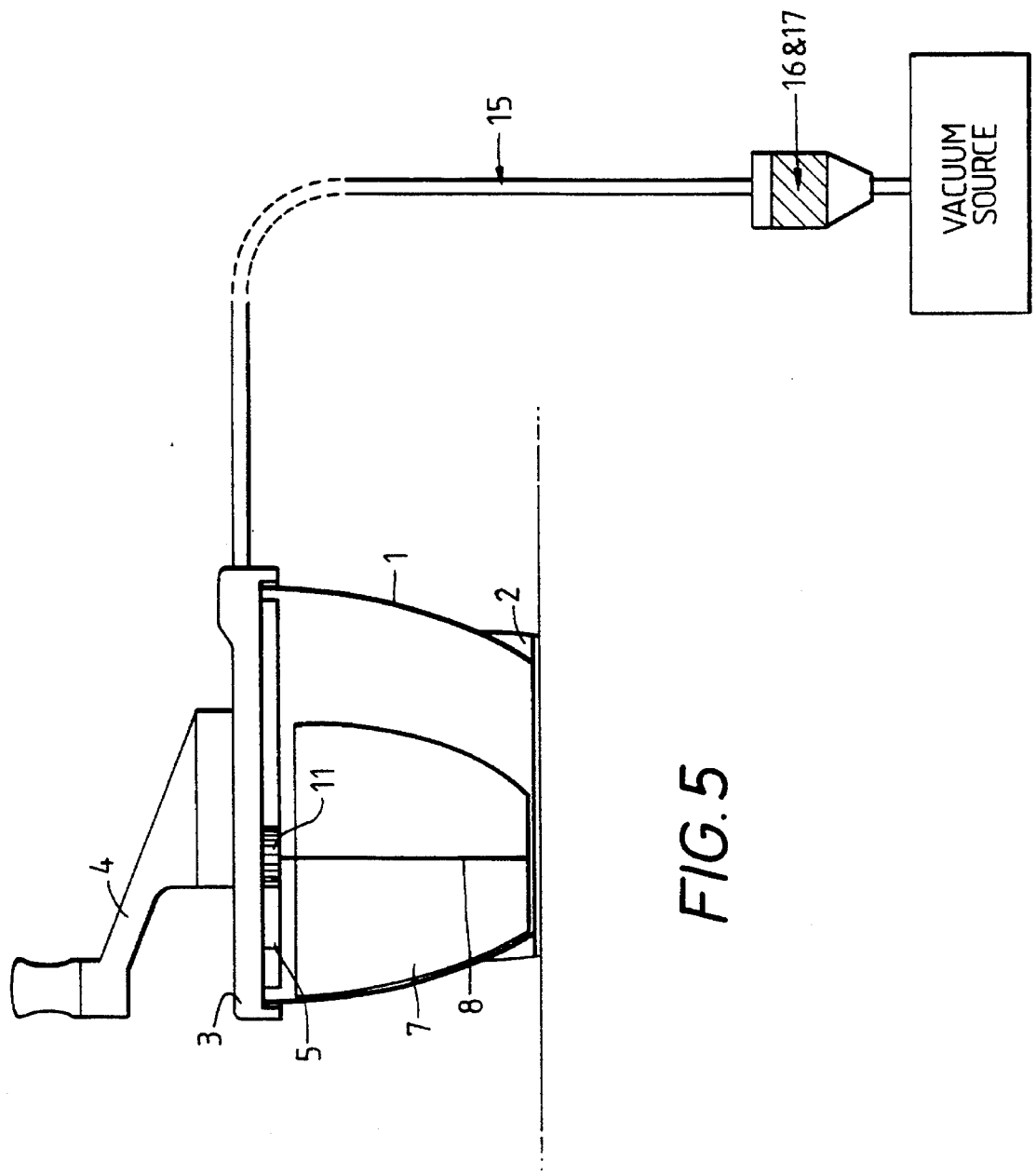
FIG. 5 shows a cross-section of a preferred embodiment of the mixing device including an integral valve/filter assembly.

Referring to FIGS. 1 to 5, the mixing device comprises a mixing bowl 1 having a base 2 and an open top. A lid 3 is adapted to fit and seal the top of the bowl 1. The lid 3 is provided with a handle 4, rotatably mounted in, and extending outwardly from the lid 3. The under side of the lid 3 is provided with a fixed, circular, toothed rack 5 which is coaxially arranged with respect to the rotation axis A of the handle. A socket 6 is provided in the underside of the handle 4, eccentrically with respect to the central axis A. The device also includes a mixing paddle 7 mounted on an axle 8 supporting mixing vanes 9 extending outwardly therefrom. The axle 8 is rotatably mounted, at one end, in the socket 6 in the handle 4. The other end of the axle 8 fits into a circular groove 10 around the base 2 of the bowl 1. A cog wheel 11 is fixedly attached to the upper part of the axle 8 for intermeshing engagement with the toothed rack 5. The lid 3 is also provided with a vacuum port 12 for connection to a vacuum pump (not shown). The lid 3 is preferably provided with a seal 13, for sealing between the lid 3 and the rim of the bowl 1, and locking means 14 to hold the lid 3 securely in place during mixing.

The substances to be mixed are placed in the mixing bowl 1. The lid 3 is then placed on the bowl and locked. The vacuum port 12 is connected, via a length of PVC tubing 15, to a vacuum pump (not shown) to create a vacuum in the bowl 1. The preferred operating vacuum is in the range of 0.7 to 0.9 bar, and is most preferably 0.75 bar. To mix the components, the operator rotates the handle 4 which causes planetary movement of the axle 8 about the central axis A and at the same time causes the cog wheel 11 to mesh with the rack 5 so to drive the cog wheel 11, producing rotation of the paddle 7 about the axis of the axle 8. Thus, due to the gear mechanism provided by the toothed rack 5 and the cog wheel 11, rotation of the handle 4 causes the paddle 7 to move around the bowl 1 in planetary fashion and, at the same time, to rotate about its own axis. Such a mechanism enables the paddle 7 to rotate several times for each turn of the handle 4 and results in a more than 90% coverage of the bowl area. One rotation of the handle 4 does not cause a whole number of rotations of the paddle 7, such that the paddle 7 is in a different orientation at the beginning and end of a particular cycle of the axle movement; this helps to avoid dead spots being formed in the cement and improves mixing.

At least one of the vanes 9 should extend from the axle 8 to the wall of the bowl 1; other vanes 9 may only extend partway across the bowl 1.

The base of the axle 8 travels around the bowl 1 in a groove 10 provided in the base 2 of the bowl to provide support, strength and stability to the paddle 7. The groove 10 ensures that the paddle 7 always remains upright and does not bend when the cement becomes thick.

The mixing bowl 1 is preferably made of clear plastic to enable the user to observe the progress of the cement as it is mixed.

During mixing, the noxious methylmethacrylate fumes are drawn off through the PVC tubing 15 and This may be done in the conventional way via a one-way valve 16, which prevents the fumes returning to the bowl 1, and an activated charcoal filter 17. Alternatively an integrated valve/filter assembly could be used which comprises a non-woven fibre material impregnated with activated charcoal. This is a much more efficient and convenient system which does not involve the use of charcoal granules.

When the cement is ready, the lid 3 is removed and the cement may be directly applied to the bone site by hand or may be transferred to a syringe for syringe application as preferred.

I claim:

1. Apparatus for manually mixing bone cement comprising means defining a hermetically sealable mixing chamber, said chamber defining means including a wall and a base, means for evacuating said chamber, said evacuating means including a port in said wall of said chamber for connection to a vacuum source to enable a vacuum to be created in said chamber, a mixing paddle extending into said chamber, said paddle defining a paddle axis of rotation, and drive means for said paddle, said drive means including a rotatable handle and gear means for coupling said handle to said paddle, rotation of said handle causing said paddle to rotate about said paddle axis and also causing simultaneous displacement of said paddle axis within said chamber whereby said paddle is moved around substantially the entire region of the interior of said chamber where the constituents of a bone cement will be located.

2. The mixing apparatus as claimed in claim 1 wherein said chamber is in the form of a bowl.

3. The mixing apparatus as claimed in claim 1 wherein said gear means comprises step-up gears such that a single rotation of said handle produces a plurality of rotations of said paddle about said paddle axis.

4. The mixing apparatus as claimed in claim 3 wherein the number of rotations of said paddle about said paddle axis produced by a single rotation of said handle is not a whole number whereby said paddle ends up in a different orientation after each single rotation of said handle.

5. The mixing apparatus as claimed in claim 1 wherein said handle defines a handle axis of rotation and wherein said gear means caused displacement comprises a single planetary rotation of said paddle axis about said handle axis of rotation during each complete rotation of said handle.

6. The mixing apparatus as claimed in claim 1 wherein said chamber defining means further comprises a lid which fits over said chamber, said lid being disposed at the opposite side of said chamber from said base.

7. The mixing apparatus as claimed in claim 6 further comprising locking means for securely holding said lid in place during mixing.

8. The mixing apparatus as claimed in claim 6 wherein said handle is rotatably mounted in said lid and extends outwardly therefrom.

9. The mixing apparatus as claimed in claim 8 wherein said paddle includes an axle, and wherein said drive means includes means for eccentrically coupling said handle to said paddle axle.

10. The mixing apparatus as claimed in claim 9 wherein said gear means comprises a circular rack fixed to the underside of said lid, and a cog wheel affixed to said paddle axle whereby said paddle axle is caused to rotate said paddle as said handle rotates.

11. The mixing apparatus as claimed in claim 1 wherein said mixing paddle comprises a shaft and at least one vane extending outwardly from said shaft, said vane being sized and shaped to sweep substantially the entire area of the interior of said chamber during the simultaneous rotation of said paddle and displacement of said paddle axis.

12. The mixing apparatus as claimed in claim 1 wherein said drive means further comprises a guide groove in said chamber base and means on said paddle for engaging said guide groove.

13. The mixing apparatus as claimed in claim 1 wherein said chamber defining means is at least partly transparent.

14. A mixing system for bone cement comprising means defining an enclosed mixing chamber, a vacuum pump, said vacuum pump communicating with said chamber for removing air from the chamber, and means for mixing the constituents of a bone cement which are delivered into said chamber, said mixing means comprising a mixing paddle, said mixing paddle defining a paddle axis of rotation, said mixing means also comprising means for manually causing rotation of said paddle about said paddle axis and simultaneously causing movement of said paddle axis within said chamber.

* * * * *